(12) United States Patent
Guederian et al.

(10) Patent No.: US 8,323,347 B2
(45) Date of Patent: Dec. 4, 2012

(54) SHOULDER PROSTHESIS

(75) Inventors: Gregory Guederian, Naples, FL (US); Zhixu Guan, Bonita Springs, FL (US)

(73) Assignee: Arthrex, Inc., Naples, FL (US)

( * ) Notice: Subject to any disclaimer, the term of this patent is extended or adjusted under 35 U.S.C. 154(b) by 1355 days.

(21) Appl. No.: 11/508,891

(22) Filed: Aug. 24, 2006

(65) Prior Publication Data

US 2007/0050040 A1 Mar. 1, 2007

Related U.S. Application Data

(60) Provisional application No. 60/710,943, filed on Aug. 25, 2005.

(51) Int. Cl.
*A61F 2/40* (2006.01)

(52) U.S. Cl. ............... 623/19.12; 623/23.47; 623/19.11; 623/22.45; 623/23.14; 623/23.23

(58) Field of Classification Search ............... 623/22.45, 623/23.11, 23.23, 23.47, 19.11
See application file for complete search history.

(56) References Cited

U.S. PATENT DOCUMENTS

| | | | | |
|---|---|---|---|---|
| 3,823,423 A | * | 7/1974 | Mercandino | 623/10 |
| 4,345,601 A | * | 8/1982 | Fukuda | 606/147 |
| 4,832,027 A | * | 5/1989 | Utz | 606/215 |
| 6,228,120 B1 | | 5/2001 | Leonard et al. | |
| 2002/0120339 A1 | * | 8/2002 | Callaway et al. | 623/19.14 |

FOREIGN PATENT DOCUMENTS

| | | |
|---|---|---|
| DE | 195 09 037 | 3/1995 |
| DE | 19509037 C1 * | 9/1996 |
| DE | 101 23 517 C1 | 11/2002 |
| DE | 10123517 C1 * | 11/2002 |
| WO | WO 01/22905 A1 | 4/2001 |
| WO | WO 02/39933 A1 | 5/2002 |

* cited by examiner

*Primary Examiner* — Thomas J Sweet
*Assistant Examiner* — Christopher D Prone
(74) *Attorney, Agent, or Firm* — Dickstein Shapiro LLP

(57) ABSTRACT

A humeral prosthesis includes a stem component and a head component joined by an inclination component. The inclination component is provided with an opening that is designed to accommodate a pair of expandable tabs extending from a side of a plate. The plate is also provided with a taper extending opposite to the pair of expandable tabs. Inclination angle, radial offset, and version are adjustable and are separately and independently set and fixed.

4 Claims, 13 Drawing Sheets

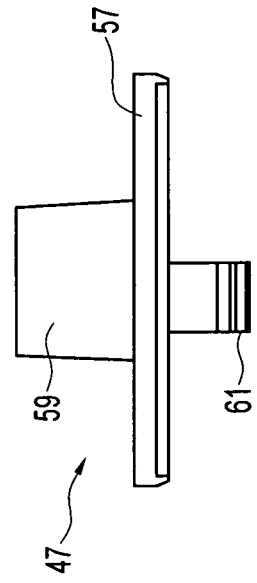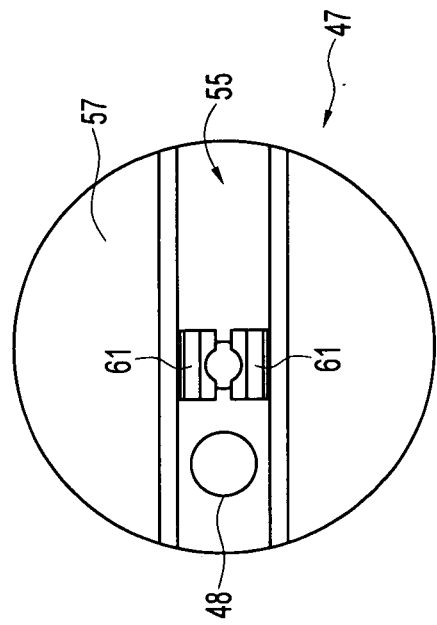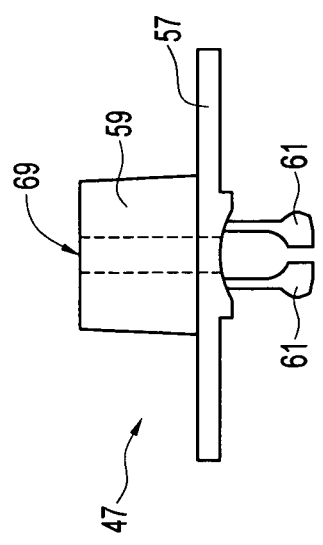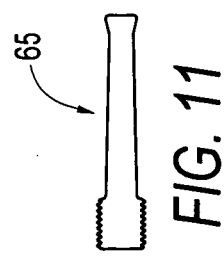

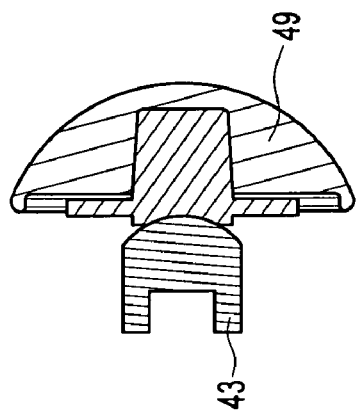
FIG. 19a SECTION B-B
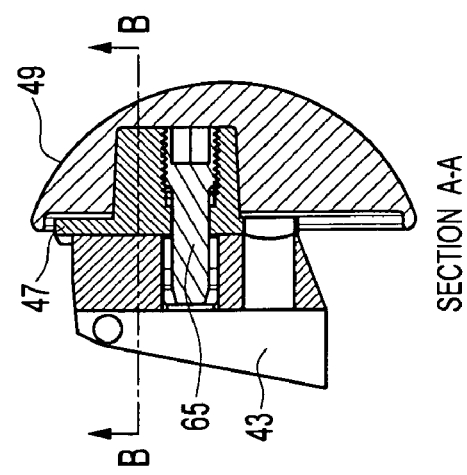
FIG. 19c SECTION A-A
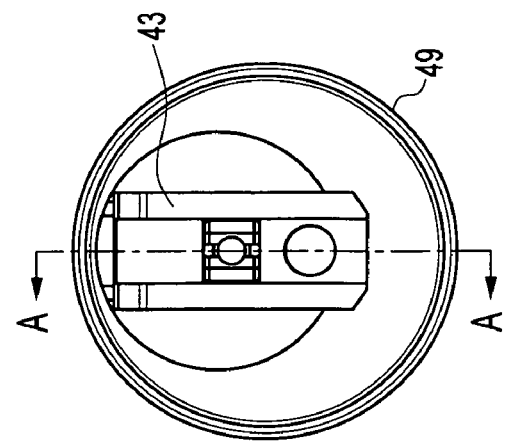
FIG. 19b

SECTION B-B

SECTION A-A

SHOULDER PROSTHESIS

CROSS-REFERENCE TO RELATED APPLICATIONS

This application claims the benefit of U.S. Provisional Application Ser. No. 60/710,943, filed Aug. 25, 2005, the entire disclosure of which is incorporated by reference herein.

FIELD OF THE INVENTION

The present invention relates to surgical reconstitution of the shoulder and, in particular, to prosthetic replacement of the humerus.

BACKGROUND OF THE INVENTION

The shoulder joint is a ball-and-socket joint with unique features that allow for exceptional freedom of movement. The hemispherical head of the humerus and the glenoid capsule of the scapula support the articular surfaces of the shoulder joint. The head of the humerus is significantly large relative to the shallow glenoid cavity. In addition, ligaments in the shoulder act largely to limit the degree of movement allowed in the joint: They do not act to maintain apposition of the joint surfaces. As a consequence of these and other special characteristics, the shoulder joint exhibits every variety of movement: flexion, extension, abduction, adduction, circumduction, and rotation. The range of movements comes as some cost to joint stability, however.

Shoulder instability and other maladies of the shoulder joint, such as arthrosis or fracture, can be sufficiently acute that prosthetic replacement of compromised joint features may be indicated. Replacement of the humeral head involves resecting the humeral head from the humerus and installing a humeral prosthetic at the resection.

Early shoulder prostheses attempted to mimic the upper portion of the humerus and extending to include the humeral head. They typically were unitary structures that included a stem to be anchored in the humeral canal and a hemispherical head to be positioned within the glenoid cavity of the scapula.

Later developments allowed for adjustments to the geometry of the prostheses. Differences in patient anatomy and surgical techniques necessitated maintaining large inventories of the early, unitary prostheses. Prostheses were kept on-hand with heads and stems of different sizes and various relative tilt angles and radial offsets.

The more-recently devised modular prostheses generally are modular systems. Their modularity allows flexibility with respect to either the tilt angle or the radial offset between the head and stem. Although some of these prior art modular systems utilize either a "standard" head or a "standard" stem, most still require a plurality of either the heads or the stems to provide complete tilt angle and radial offset flexibility. None of the prior art systems provides complete tilt angle and radial offset flexibility without requiring different modular head or stem components of each given size. As a result, substantial inventories are maintained of either the stems or heads, which are the most expensive components. Moreover, most of the known systems provide incomplete adjustability of prosthetic geometry.

FIG. 1 illustrates a modular humeral-prosthesis 1 disclosed in DE 19509037 to Habermeyer. The humeral-prosthesis 1 allows for adjustment of radial offset, inclination angle, and version (anteversion/retroversion). Humeral-prosthesis 1 includes a stem-module 3 that features a shank 5 having an upper-shank portion 7 and a tongue/tab 9 that supports a pin 11. Pin 11 hinges an angle-adapter 13 to the rest of the stem-module 3. Angle-adapter 13 fits over tongue/tab 9 and pivots on pin 11 through an inclination angle a as shown in FIG. 2. The angle-adapter 13 can be locked in place to retain a desired inclination angle.

Humeral-prosthesis 1 also includes a coupling adapter 17, shown in FIGS. 1-4. The coupling adapter 17 is shown in FIG. 3 separated from other prosthetic components. The coupling adapter 17 includes an adapter plate 27. A male Morse taper 29 extends from one side of adapter plate 27. A ball joint 31 extends from the adapter plate 27 on the side opposite the male Morse taper 29. The ball joint 31 is located eccentrically on the adapter plate 27. The eccentricity of the ball joint 31 on the adapter plate 27 allows for adjustment of a radial offset between the prosthetic stem 3 and a spherical cap 27 secured to the male Morse taper 29, as described further below. Once established, the radial offset is fixed using set screw 23 (FIG. 4).

Referring to FIG. 5, adjustment of anteversion/retroversion is provided by the angle-adaptor 13. As discussed above, the angle adaptor 13 pivots on the axis 11 at the top end 7 of the stem 3 to adjust the inclination angle a. In the view of FIG. 5 it can be seen that the angle adapter 13 is beveled at its interface with coupling adapter 17. The beveling allows the adapter 13, and hence the stem 3, to pivot by way of ball joint 31 with respect to the coupling adapter 17. The stem 3 and coupling adapter 17 rock through an angle b to one face 15 or the other of coupling adapter 17. Faces 15 on coupling adapter 17 act as stops to define the maximum pivot to either side. Set screw 23, used to retain the desired radial offset, also fixes the desired version.

A need exists in the prior art for a modular shoulder prosthesis that features universal setting of radial-offset, inclination angle, and anteversion/retroversion, with independent fixing of each setting.

SUMMARY OF THE INVENTION

The present invention provides a humeral prosthetic and surgical methods for reconstitution of a shoulder joint. The humeral prosthetic allows universal adjustment to the prosthetic inclination angle, radial offset, and version. In an exemplary embodiment, the humeral prosthetic includes three components: (i) a stem for attachment to the humerus, (ii) a spherical head for replacing the humeral head, and (iii) a coupling adapter joining the stem and the spherical head. At least one of the settings for the three adjustments noted above may be fixed independently of the other two settings. Preferably, a setting for each of the three adjustments is fixed independently.

In an exemplary embodiment, each modular component includes means for setting and fixing a respective one of the three adjustments noted above. More specifically, the exemplary prosthetic stem includes means for setting and fixing the inclination angle of the prosthesis. The exemplary spherical head includes means for setting and fixing the radial offset. The coupling adapter includes means for setting and fixing version.

The present invention also provides a method of conducting surgery by: (i) providing a humeral prosthetic comprising a humeral attachment; an adapter comprising a plate, a taper extending from a first side of the plate, a concavity formed along a diameter on a second side of the plate, and an expandable locking component extending from the second side of the plate; and a spherical head; (ii) providing the humeral prosthetic within a patient's humerus; and (iii) independently adjusting at least one of the radial offset of the spherical head, the inclination angle of the humeral attachment, and the version of the adapter, relative to the other two.

These and other features and advantages of the invention will be more apparent from the following detailed description that is provided in connection with the accompanying drawings and illustrated exemplary embodiments of the invention.

BRIEF DESCRIPTION OF THE DRAWINGS

FIG. 8 shows a coupling adapter viewed in elevation according to the invention;

FIG. 9 shows the coupling adapter of FIG. 8 viewed in side elevation;

FIG. 10 shows details of the coupling adapter of FIGS. 8 and 9;

FIG. 11 illustrates a locking screw according to the invention;

FIG. 12 illustrates another locking screw according to the invention;

FIGS. 19(a)-(c) illustrate schematic views of the prosthesis of FIG. 18(b);

DETAILED DESCRIPTION OF THE PREFERRED EMBODIMENTS

The invention provides a humeral prosthetic and surgical methods for reconstitution of a shoulder joint. The humeral prosthetic allows universal adjustment to the prosthetic inclination angle, radial offset, and version. In an exemplary embodiment, the humeral prosthetic includes three components: a stem for attachment to the humerus, a spherical head for replacing the humeral head, and a coupling adapter joining the stem and the spherical head, wherein at least one of the settings for the three adjustments noted above may be fixed independently of the other two settings. Preferably, a setting for each of the three adjustments is fixed independently.

In an exemplary prosthesis and as detailed below, each modular component includes means for setting and fixing a respective one of the three adjustments noted above. More specifically, the exemplary prosthetic stem includes means for setting and fixing the inclination angle of the prosthesis. The exemplary spherical head includes means for setting and fixing the radial offset. The coupling adapter includes means for setting and fixing version.

The invention also provides a method of surgical reconstruction of shoulder by: (i) providing a humeral prosthetic comprising a humeral attachment; an adapter comprising a plate, a taper extending from a first side of the plate, a concavity formed along a diameter on a second side of the plate, and an expandable locking component extending from the second side of the plate; and a spherical head; (ii) providing the humeral prosthetic within a patient's humerus; and (iii) independently adjusting at least one of the radial offset of the spherical head, the inclination angle of the humeral attachment, and the version of the adapter, relative to the other two.

Figure 1:
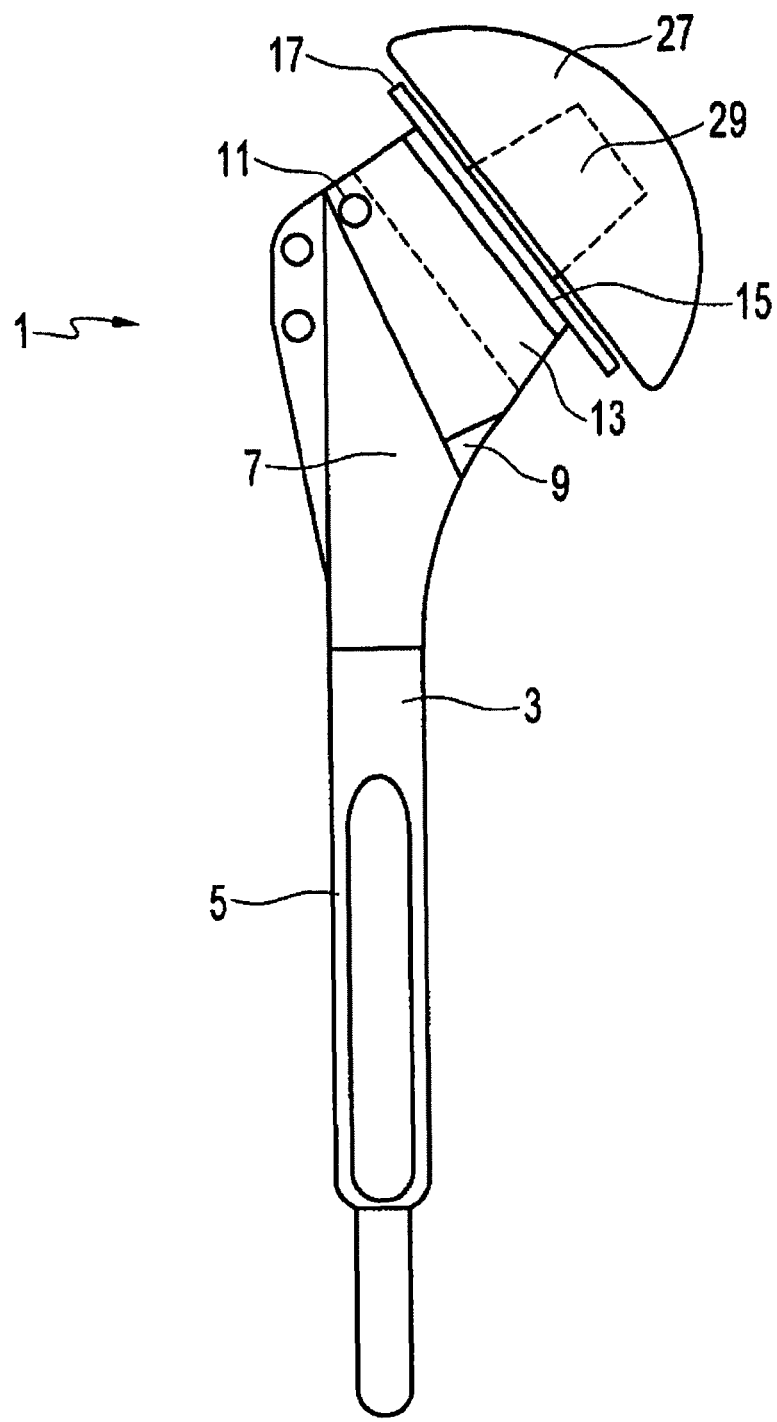
FIG. 1 illustrates a prior art prosthesis shown in anterior/posterior elevation.
Figure 2:
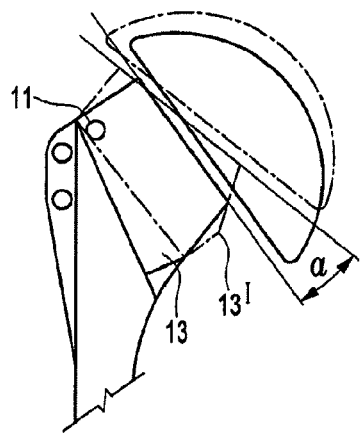
FIG. 2 is a detailed view of the upper portion of the prior art prosthesis illustrating adjustment of the inclination angle.
Figure 3:
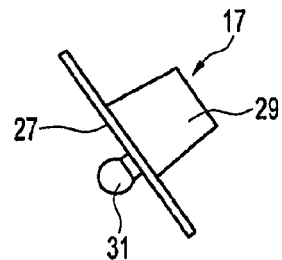
FIG. 3 is a side view of an adapter portion of the prior art prosthesis shown in FIGS. 1 and 2.
Figure 4:
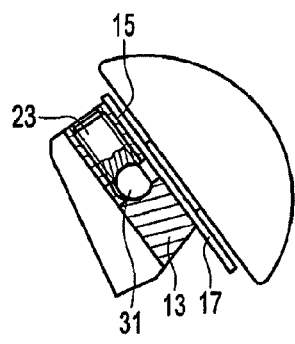
FIG. 4 is a partial cut-away view illustrating details of the upper portion of the prior art prosthesis shown in FIG. 2.
Figure 6:
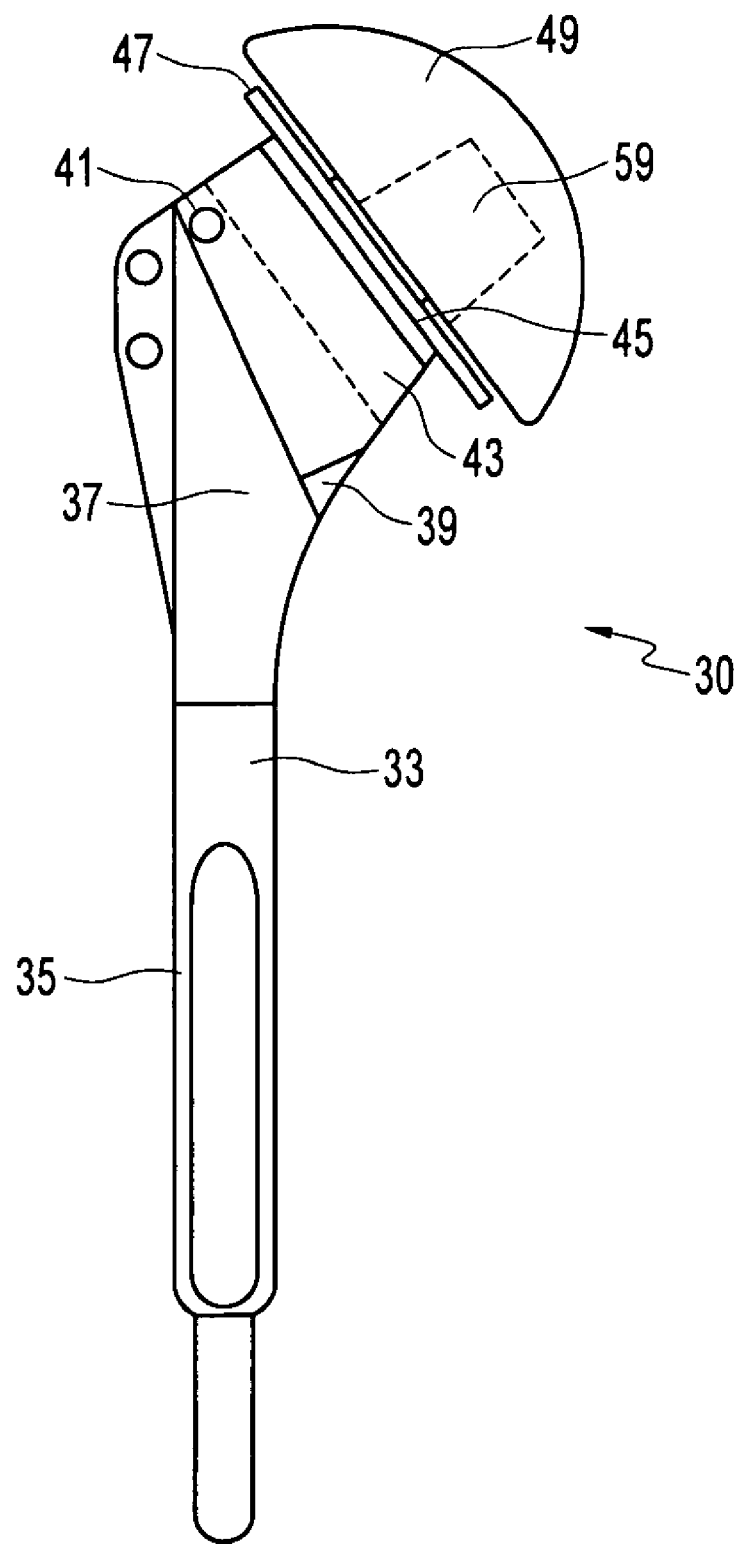
FIG. 6 illustrates a humeral prosthesis according to an exemplary embodiment of the present invention.

Referring now to the drawings, where like elements are designated by like reference numerals, FIG. 6 illustrates an exemplary humeral prosthesis according to an exemplary embodiment of the invention. FIG. 6 illustrates modular humeral-prosthesis 30 including a stem-module 33 that features a shank 35 having an upper-shank portion 37 and a tongue/tab 39 that supports a pin 41. Pin 41 hinges an inclination component 43 to the rest of the stem-module 33. Inclination component 43 fits over tongue/tab 39 and pivots on pin 41 through an inclination angle a as shown in FIG. 2 illustrating the prior art prosthesis. The inclination component 43 includes an opening 44 (FIG. 7) that provides access to a screw (not shown) threaded between a pair of spreadable leaves formed in a portion of the tongue/tab 39. The spreadable leaves are spread progressively further apart by advancement of the screw and into locking frictional engagement with opposing inside surfaces of the inclination component 43. The screw is advanced by turning sufficient to fix the position of the inclination component 43 at a desired inclination angle.

Figure 7:
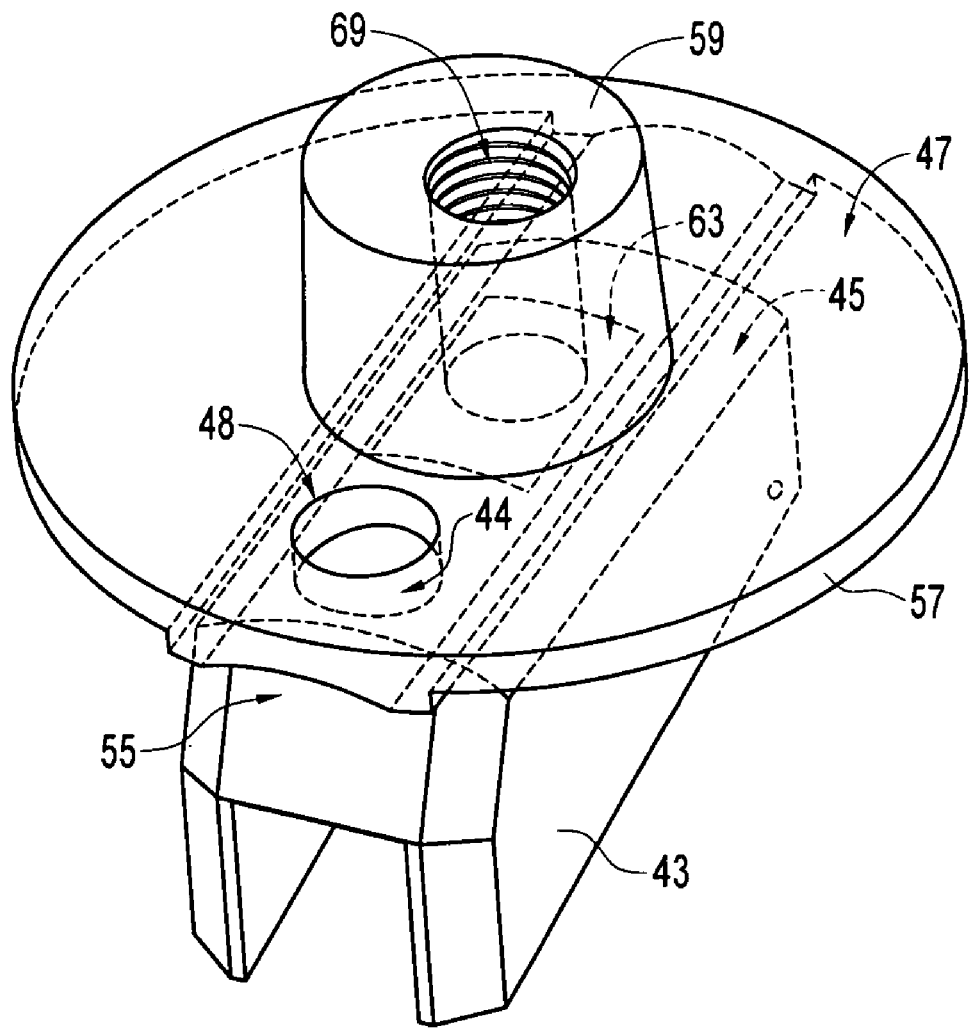
FIG. 7 illustrates an angle adapter and a coupling adapter enlarged to show detail.

Humeral-prosthesis 30 also includes coupling adapter 47, shown in FIGS. 6-10. The coupling adapter 47 is shown in FIG. 7 paired with the inclination component 43. The coupling adapter 47 includes an adapter plate 57. An access opening 48 through the adapter plate 57 corresponds to the opening 44 in the inclination component 43 and provides access to the inclination-angle locking screw discussed above. A male Morse taper 59 extends from one side of adapter plate 57. Morse taper 59 locks into a female Morse taper 49a formed in spherical head 49. A shallow, elongate concavity 55 extends along a diameter of adapter plate 57 on a side opposite the male Morse taper 59. The elongate concavity 55 complements an elongate convex surface 56 formed on inclination component 43, discussed in further detail below.

FIGS. 8-10 further illustrate details of coupling adapter 47. A pair of clothespin tabs 61 extends from adapter plate 57.

The clothespin tabs are accepted into a rectangular opening 63 formed in inclination component 43. A pre-installed locking screw 65 (FIG. 11) or 67 (FIG. 12) is urged within tapped hole 69 between clothespin tabs 61. The locking screw 65, 67 wedges between clothespin tabs 61. The clothespin tabs 61 spread apart to frictionally-engage inner walls of rectangular opening 63 with sufficient force to fix a relative versional position between inclination component 43 and coupling adapter 47. In an exemplary embodiment, clothespin tabs 61 may have a square configuration to lock within rectangular opening 63 and to prevent rotation within the inclination block. However, the invention is not limited to this exemplary embodiment, and contemplates additional shapes and geometries for the clothespin tabs 61, for example, a rectangular or trapezoidal configuration among many others.

Figure 5:
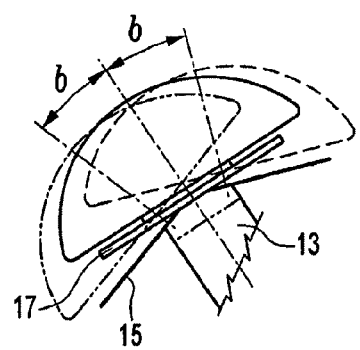
FIG. 5 is a detailed view from above the prosthesis illustrating the beveled faces allowing adjustment of version in the prior art prosthesis shown in FIGS. 1-4.

More specifically, version is adjusted by pivoting adapter plate 57 with respect to inclination component 43. The components will pivot through angles b of retroversion and anteversion as illustrated in FIG. 5 showing a prior art prosthesis. Instead of pivoting around a bevel, however, elongate concavity complements convex surface 45 so that the two are mutually engaged throughout the range of motion from +b to −b, the range being determined by the fit of clothespin-tabs 61 within rectangular opening 63. Once the desired version is achieved, one of the locking screws 65, 67 is used to spread the clothespin tabs into locking engagement with inside surfaces delimiting rectangular opening 63.

Referring again to FIG. 6, the female Morse taper socket is formed eccentric to a central axis of the spherical head 49. Radial offset is adjusted by rotating the spherical head 49 around male Morse taper 59 with respect to coupling adapter 47. The radial offset is fixed in position by the locking interaction of the complementary Morse taper features.

Figure 13:
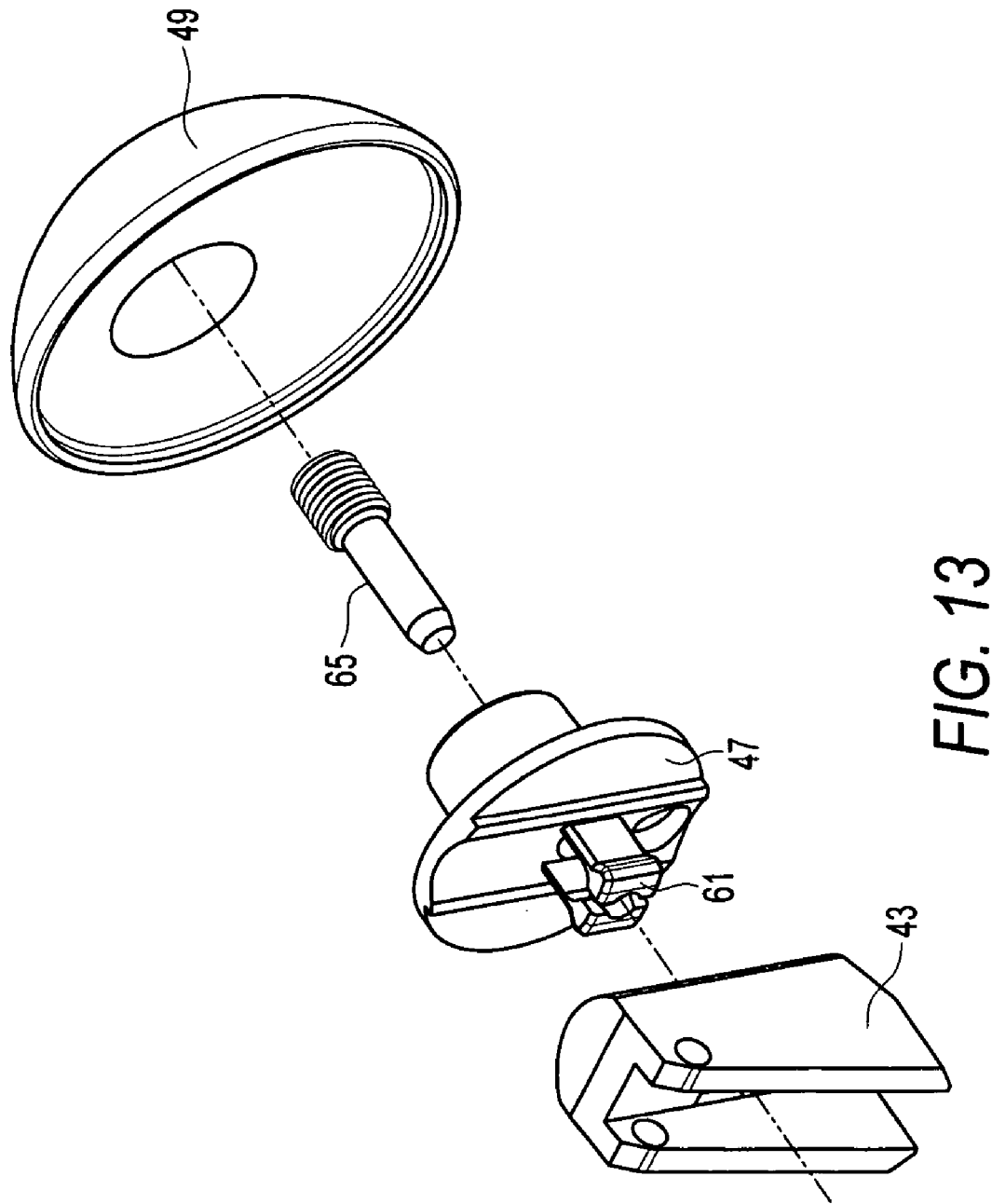
FIG. 13 illustrates an exploded view of the prosthesis of the present invention, including an inclination component, a coupling adapter, a screw and a spherical head.
Figure 14:
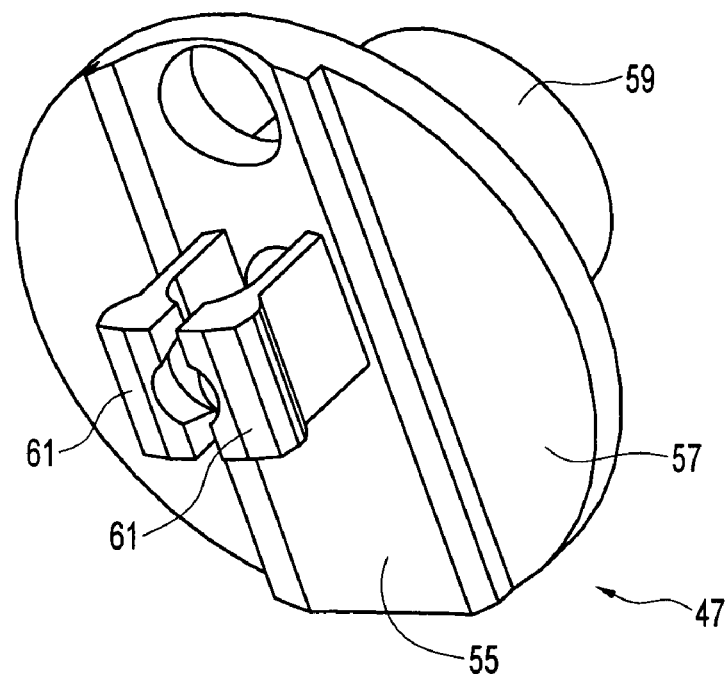
FIG. 14 illustrates a perspective view of the coupling adapter of FIG. 13.
Figure 15:
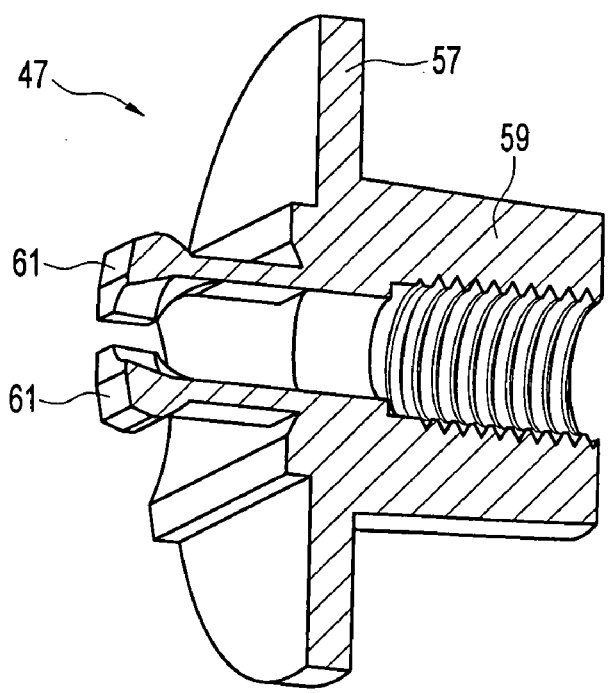
FIG. 15 illustrates a perspective cross-sectional view of the coupling adapter of FIG. 14.
Figure 16:
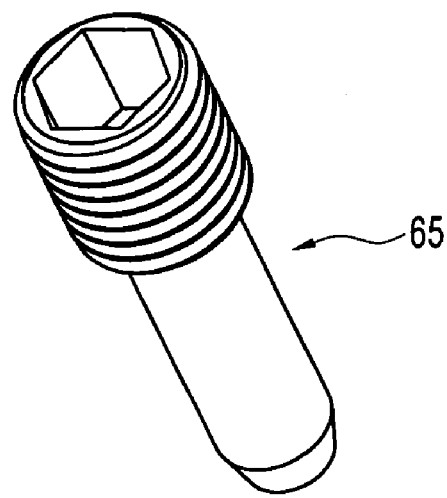
FIG. 16 illustrates a perspective view of the screw of FIG. 13.
Figure 17:
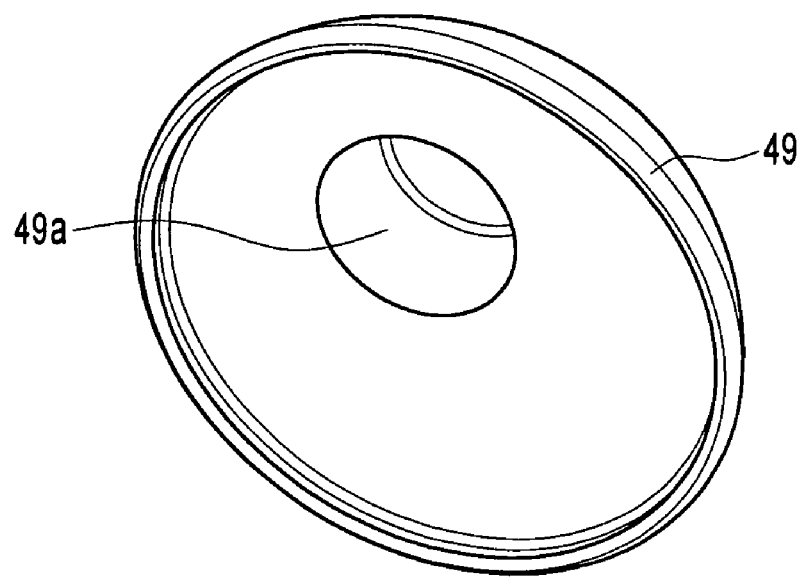
FIG. 17 illustrates a perspective view of the spherical head of FIG. 13.
Figure 18B:
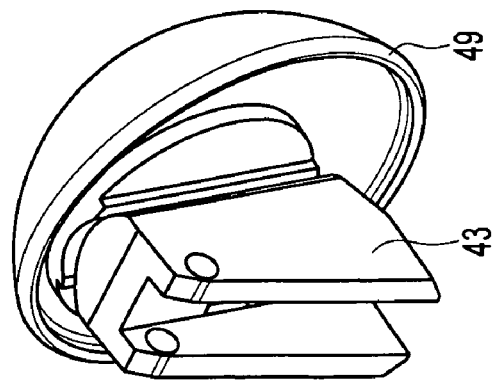
FIG. 18(b) illustrates the prosthesis of FIG. 18(a)
Figure 18A:
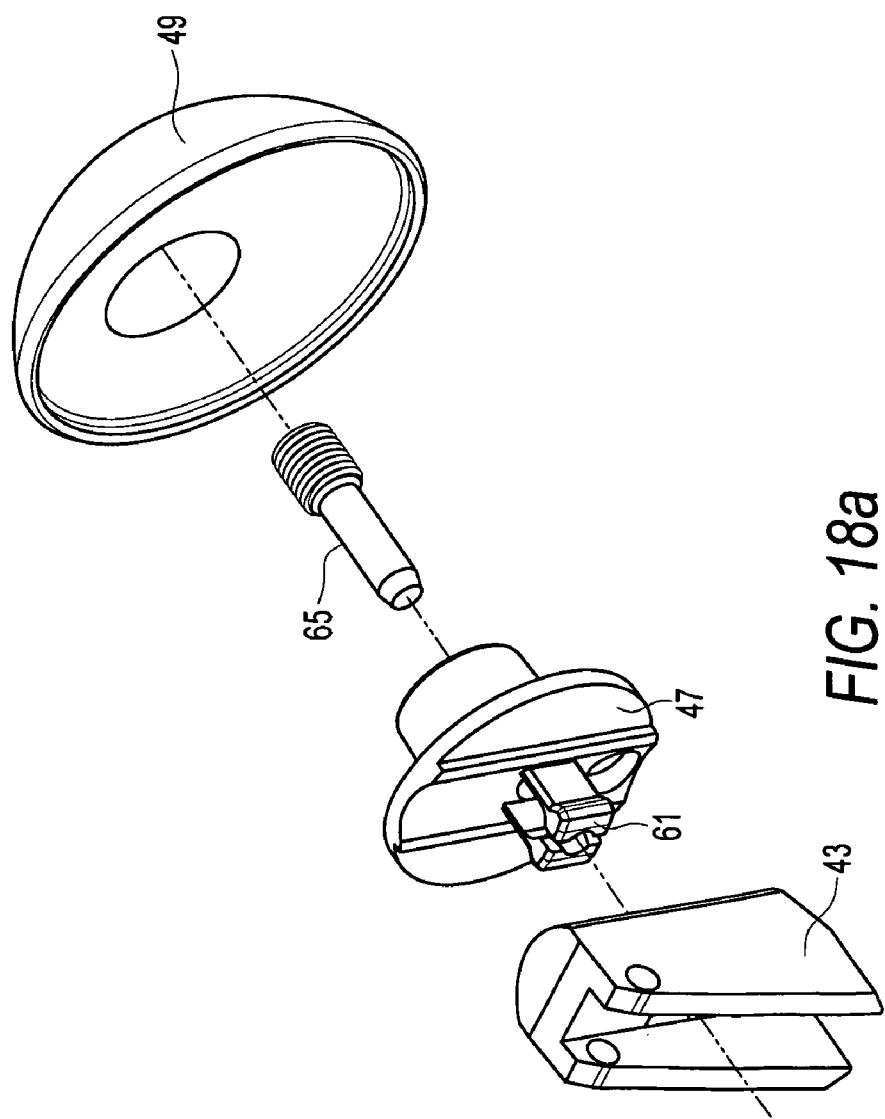
FIG. 18(a) illustrates an exploded schematic view of the prosthesis of the present invention, including an inclination component, a coupling adapter, a screw and a spherical head.
Figure 20B:
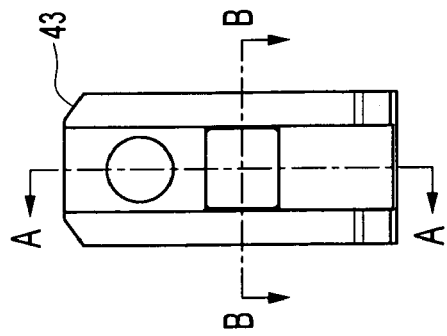
FIGS. 20(a)-(d) illustrate schematic views of the inclination component of the prosthesis of FIG. 18(b)
Figure 20D:
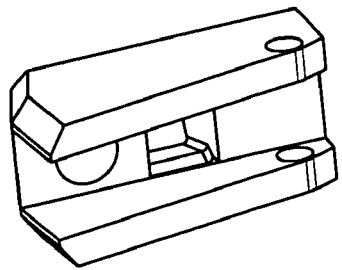
Figure 20A:
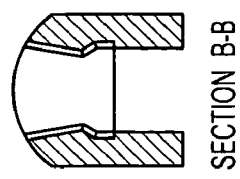
Figure 20C:
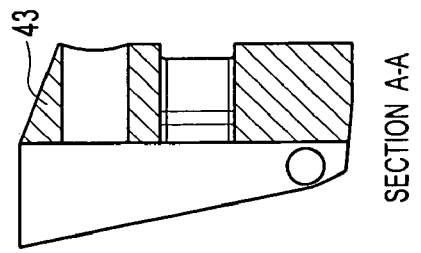
Figure 21E:
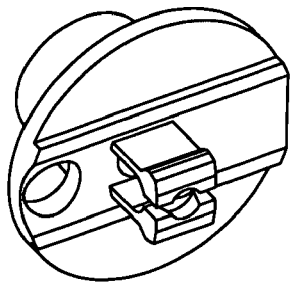
FIGS. 21(a)-(e) illustrate schematic views of the coupling adapter of the prosthesis of FIG. 18(b)
Figure 21B:
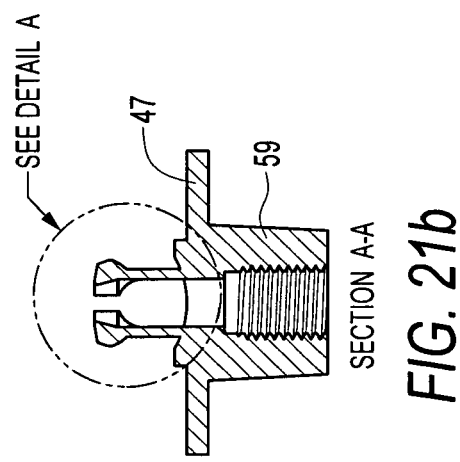
Figure 21D:
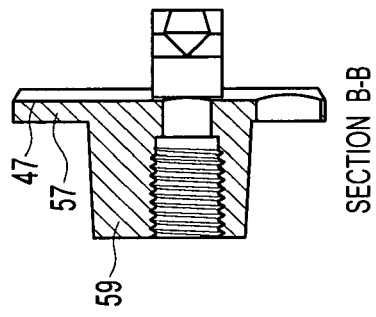
Figure 21A:
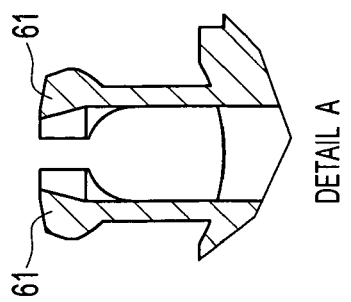
Figure 21C:
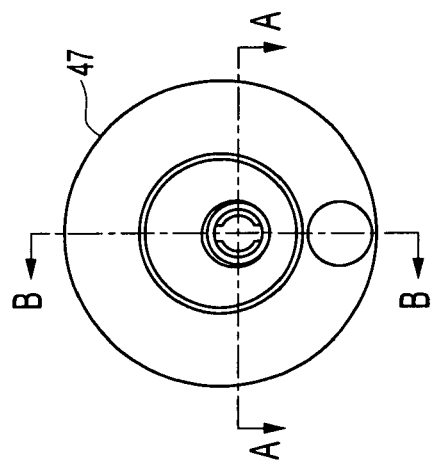
Figure 22A:
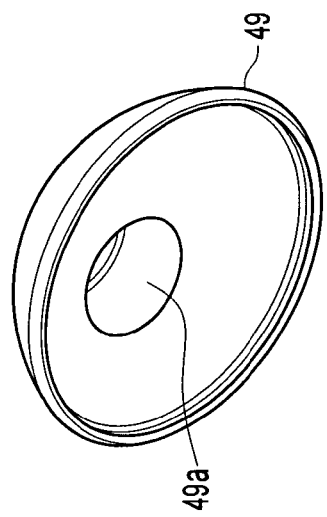
FIGS. 22(a)-(e) illustrate schematic views of the spherical head of the prosthesis of FIG. 18(b).
Figure 22E:
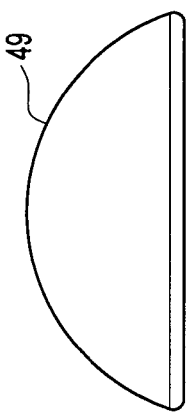
Figure 22D:
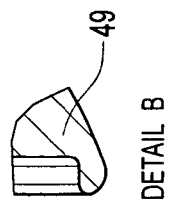
Figure 22C:
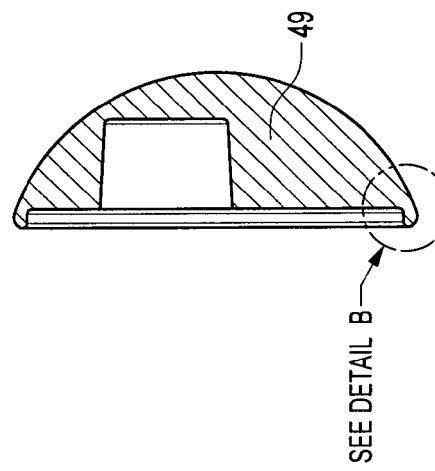
Figure 22B:
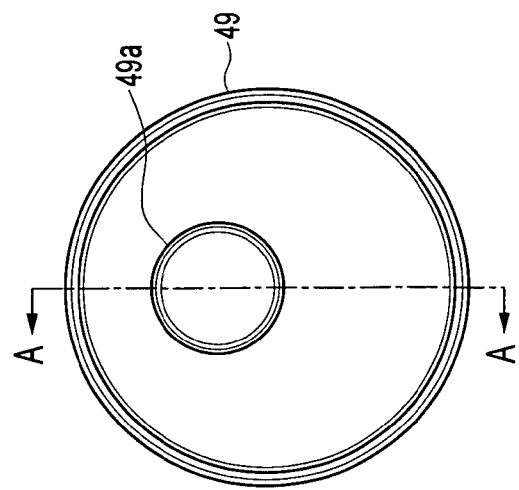

FIG. 13 illustrates a an exploded view of the prosthesis of the present invention, comprising inclination component 43, coupling adapter 47 with clothespin tabs 61, locking screw 65 and spherical head 49. Coupling adapter 47 is further detailed in FIGS. 14 and 15, which illustrate a perspective view and a perspective cross-sectional view, respectively, of the coupling adapter. FIG. 16 illustrates a perspective view of locking screw 65 while FIG. 17 illustrates a perspective view of the spherical head 49.

FIGS. 18-22 illustrate additional schematic views of the prosthesis of the present invention, comprising inclination component 43, coupling adapter 47 with clothespin tabs 61, locking screw 65 and spherical head 49.

The above description and drawings illustrate preferred embodiments which achieve the objects, features and advantages of the present invention. It is not intended that the present invention be limited to the illustrated embodiments. Any modification of the present invention which comes within the spirit and scope of the following claims should be considered part of the present invention.

What is claimed as new and desired to be protected by Letters Patent of the United States is:

1. A humeral prosthetic, comprising:
    a humeral attachment including an inclination component for setting and fixing an inclination angle, the inclination component having a first opening for receiving a first screw threaded between a pair of spreadable leaves formed in a portion of a tongue/tab, wherein the leaves are spread progressively apart by advancement of the first screw into locking frictional engagement with opposing inside surfaces of the inclination component, the inclination component having an elongate convex surface;
    an adapter for setting a version, the adapter comprising a plate having a male Morse taper extending from one side thereof and an elongate concavity extending along a diameter of the adapter plate on a side opposite the male Morse taper, the elongate concavity complementing the elongate convex surface of the inclination component, the plate including an expandable locking component with a pair of tabs extending therefrom, the pair of tabs being accepted into a second opening formed in the inclination component, wherein the tabs spread apart to frictionally engage inner walls of the second opening for adjustment and fixing of the version between the inclination component and the adapter, the version being adjusted by pivoting the adapter plate with respect to the inclination component, with the elongate concavity of the plate complementing the elongate convex surface of the inclination component throughout a range of motion determined by the tabs frictional engaged within the second opening of the inclination component, and wherein a second screw is used to spread the tabs into locking engagement with the inside surfaces of the second opening to fix the version; and
    a spherical head having a female Morse taper for locking onto the male Morse taper of the adapter, wherein radial offset is adjusted by rotating the spherical head around the male Morse taper of the adapter, the radial offset being fixed in position by locking interaction of the complementary Morse tapers of the spherical head and the adapter wherein each of the inclination angle, version, and radial offset, is fixed independently of the other two.

2. The humeral prosthetic of claim 1, wherein the pair of tabs has a clothespin configuration.

3. The humeral prosthetic of claim 1, wherein the plate of the adapter has an access opening corresponding to the first opening in the inclination component for providing access to the first screw.

4. The humeral prosthetic of claim 1, wherein the second opening is rectangular.

* * * * *